United States Patent [19]

Steer

[11] Patent Number: 4,710,183

[45] Date of Patent: Dec. 1, 1987

[54] OSTOMY APPLIANCE

[75] Inventor: Peter L. Steer, Surrey, England

[73] Assignee: Craig Medical Products Ltd., Sussex, England

[21] Appl. No.: 860,695

[22] Filed: May 2, 1986

Related U.S. Application Data

[63] Continuation of Ser. No. 664,726, Oct. 25, 1984, abandoned.

[30] Foreign Application Priority Data

Nov. 1, 1983 [GB] United Kingdom ................. 8329121

[51] Int. Cl.[4] .............................................. A61F 5/44
[52] U.S. Cl. .................................................. 604/344
[58] Field of Search ............................... 604/332–345

[56] References Cited

U.S. PATENT DOCUMENTS 3,095,995 7/1963 Foster ......................... 16/DIG. 13
3,289,877 12/1966 Wolf ............................... 16/225 X
3,628,215 12/1971 Everburg .............................. 16/293

FOREIGN PATENT DOCUMENTS 2101249 1/1983 United Kingdom .

Primary Examiner—Harland S. Skogquist
Attorney, Agent, or Firm—Lawrence S. Levinson; Robert E. Lee, Jr.

[57] ABSTRACT

An improved ostomy appliance has two interengageable coupling elements, one of which (herein called the body side coupling element) is secured to a medical grade adhesive pad and the other side of which is secured to an ostomy bag. A flexible chute ring is interposed between the body side coupling element and the adhesive pad. The flexible chute ring is attached to a polymeric film surface of the pad at a first annular region and to the body side coupling element at a second annular region. The first annular region is located radially inwardly of the coupling element.

12 Claims, 8 Drawing Figures

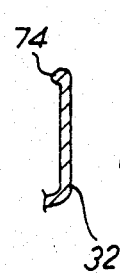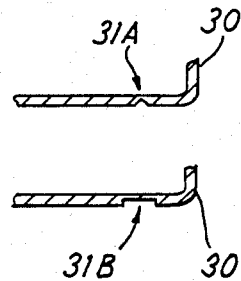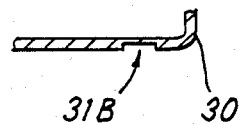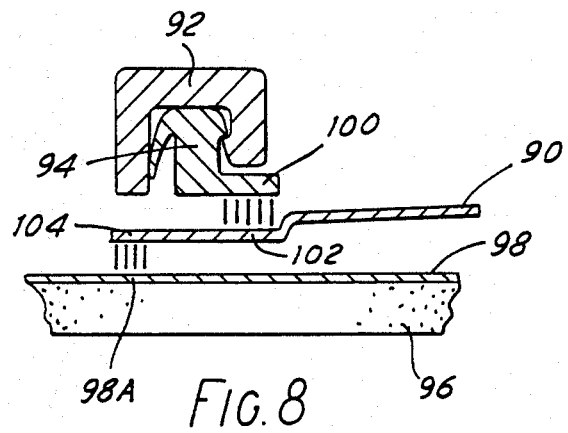

OSTOMY APPLIANCE

This is a continuation of co-pending application Ser. No. 664,726 filed on Oct. 25, 1984, abandoned.

BACKGROUND OF THE INVENTION

This invention relates to an ostomy appliance.

The ostomy appliance shown in British Patent Spec. No. 1 571 657 has received wide acceptance and approval among those persons needing to wear an ostomy bag. It has been realized more recently (see British Patent Application No. 2 115 288) that it can be desirable to provide an appliance with enhanced flexibility so that any possible discomfort to the wearer is minimized. Furthermore, many current designs of ostomy appliance exhibit crevices or other zones where discharged faecal material can stick or accumulate. This is readily seen to be undesirable as it means that bag changing is necessarily a messy and unhygienic operation.

SUMMARY OF THE INVENTION

It is an aim of the present invention to provide an improved ostomy appliance of the type which has two interengagable coupling elements, one of which (herein called the body side coupling element) is, or can be, secured to a medical grade adhesive pad and the other side of which is, or can be, secured to an ostomy bag.

According to the present invention, a flexible chute ring is interposed between the body side coupling element and the adhesive pad.

With such an arrangement, a chute portion of the ring entirely eliminates or greatly reduces the chance that particles of discharged matter will become lodged on or in the bag side coupling element, and the said element and the pad can be joined together in such a way as to facilitate coupling and uncoupling of the appliance in a manner which minimizes discomfort to the wearer.

According to an advantageous feature of the invention, the flexible chute ring is secured to the adhesive pad at a first annular region which is radially inwardly of the coupling element at a second annular region which is radially outwardly of the first annular region. According to a preferred feature of this embodiment of the invention, the second annular region has a greater radial extent than the first. This leads to the desirable result that the flexible chute ring can flex at a region just radially outwardly of the first annular region so allowing a wearer to get his fingers or thumb behind the chute ring and between the latter and the adhesive pad.

BRIEF DESCRIPTION OF THE DRAWINGS

The invention will be better understood from the following non-limiting description of examples thereof given with reference to the accompanying drawings in which:

FIG. 5 is a part-sectional view of an optional but advantageous version of the rim end of the chute ring showing an external peripheral pip or bump located to substantially coincide with an edge of a bag side coupling element which is innermost, relative to the bag, the pip or bump serving two purposes, namely to help to hold the flexible chute ring in its assembled position and secondly to help to close off any crevice existing between the bag side coupling element and the bag wall to which it is secured;

FIGS. 6 and 7 illustrate, on a smaller scale, alternative configurations of flexible chute ring, and FIG. 8 is a diagrammatic illustration of a possible method of manufacture of an ostomy appliance showing an alternative (but presently less preferred) design of flexible ring, and indicating the sequence of welding steps; in the illustration the body side coupling element is shown for clarity, but in fact, in the manufacture, the bag side coupling element alone would be welded to the intervening flexible ring.

DETAILED DESCRIPTION OF THE DRAWINGS

Figure 1:
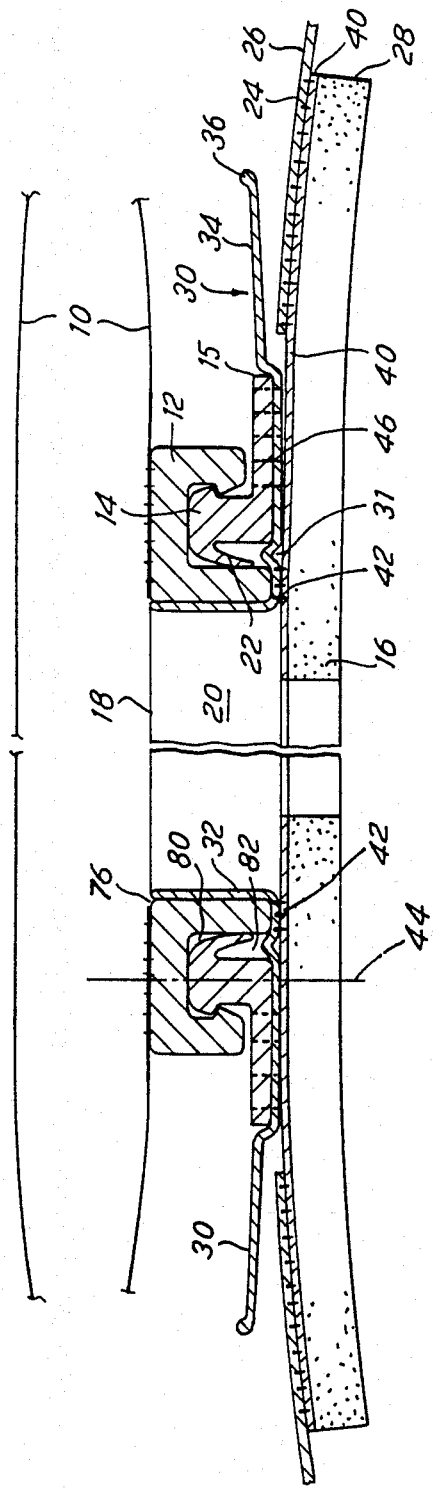
FIG. 1 is a diagrammatic axial cross-section through one example of ostomy appliance in accordance with the invention.

In the drawing, like parts are indicated by like reference numerals.

Referring firstly to FIG. 1, the illustrated ostomy appliance includes a bag 10, a bag side coupling element 12, a body side coupling element 14, and a pad 16 of medical grade adhesive, such as pressure sensitive adhesive formulations that consist of a homogenous blend of one or more water soluble or water swellable hydrocolloids dispersed in a viscous elastomeric substance such as polyisobutylene as disclosed by Chen in U.S. Pat. No. 3,339,506. Optionally, the adhesive composition can also include one or more cohesive strengthening agents described by Chen et al. in U.S. Pat. No. 4,192,785 or one or more hydratable natural or synthetic polymers as described by Pawelchak et al. in U.S. Pat. No. 4,393,080. Other medical grade adhesives designed for ostomates and available on the market are also suitable.

The ostomy bag 10 has stomal aperture 18 in its body side wall, and the bag 10 is fixed in any suitable manner for example by a plastics welding operation to the bag side coupling element 12 with the aperture 18 in registry with the stomal orifice 20 which is defined by the coupling elements. The coupling elements 12 and 14 are constructed to interengage and the element 14 has a deflectable sealing skirt 22. For a fuller description of these features, the reader is referred to British Patent Specifications Nos. 1 568 860 and 1 571 657.

The outer periphery of the medical grade adhesive pad 16 has welded thereto, by a weld 24, an annular cover sheet 26 which serves to cover the outer edge 28 of the adhesive pad 16.

According to the present invention, a flexible chute ring 30 is interposed between the body side coupling element 14 and the adhesive pad 16. The ring 30 has a chute portion 32 and a flange portion 34. As illustrated it also has an outer marginal bead 36 but this is not essential. The flexible chute ring 30 also has a zone of weakening or increased flexibility 31, which may be constituted by the bend 31 as shown in FIG. 1, by a notch 31a as shown in FIG. 7 or by a thin region 31b as shown in FIG. 7 can equally well be used. The purpose of the zone of weakening or zone of increased flexibility 31 is to facilitate some bending of the flexible chute ring so that a wearer can interpose a finger of a thumb as shown in the FIG. 2 between the pad 16 and the ring 30. This is of particular assistance when coupling the coupling elements 12 and 14 together.

Figure 2:
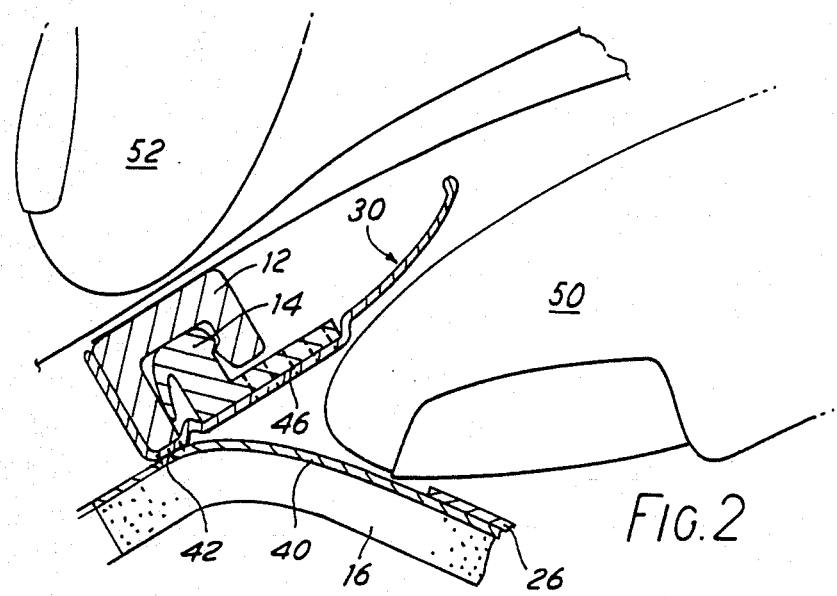
FIG. 2 is a view showing coupling by the wearer of a bag and bag side coupling element to a pad and body side coupling element, using a finger and thumb, and illustrating how the chute ring enables the wearer to get his thumb under an outer peripheral portion of a flange on the body side coupling element.

A thin layer of polymeric film 40 advantageously covers the adhesive pad 16, this being present so that other parts can be secured to the pad 16 by plastics welding operations. According to an advantageous feature of the present invention, the flexible chute ring 30 is secured to the film 40 and hence to the pad 16 by a plastics welding operation at a first annular region 42 which is radially inwardly of the ring 30, with reference to the coupling axis 44. In FIGS. 1 and 2 the plastics weld is diagrammatically represented by vertical lines. Also according to an advantageous feature of the invention, the flexible chute ring 30 is secured to the body side coupling element 14 by a plastics welding operation at a second annular region 46.

The region 46 is radially outwardly of the region 42. As can be seen from FIGS. 1 and 2, the radial extent of the weld region 46 is greater than the radial extent of the weld region 42. The lesser the radial extent of the weld region 42, the easier is the thumb insertion illustrated in FIG. 2, but naturally a sufficient radial extent of weld 42 must be employed to give security of attachment between the film 40 and the ring 30. In FIG. 2, a wearer is seen connecting the coupling elements 12 and 14 by pressure between 50 and index finger 52.

Figure 3:
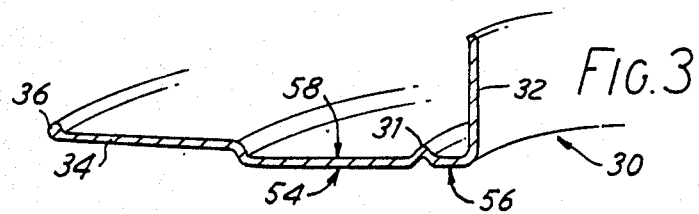
FIG. 3 shows the cross-sectional shape of one preferred form of flexible chute ring.

FIG. 3 illustrates the flexible chute ring 30 having a chute portion 32, a zone of increased flexibility 31, a flange 34 and a marginal bead 36. There is a step configuration between the flange portion 34 and an inner portion generally indicated at 54. The surface 56 is that which is welded to the film 40 whereas the surface 58 is that which is welded to a flange of the body side coupling element 14.

Figure 4:
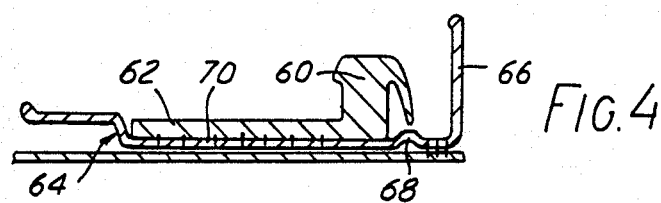
FIG. 4 is a cross-sectional detail view showing part of an alternative configuration for the flexible chute ring.

FIG. 4 shows an alternative version of flexible chute ring, the ring shown in FIG. 4 being suitable for use with the body side coupling element 60 having a flange 62 which is radially more extensive than the flange 15 of the body side coupling element 14. The ring 64 shown in FIG. 4 has chute portion 66, an increased flexibility zone of weakening 68, and an annular flange region 70 which is welded to the flange 62 of the coupling element 60. The manner of operation use of the flexible chute ring 64 is similar to that of the ring illustrated in FIGS. 1 and 2.

FIG. 5 illustrates the formation in which the chute portion 32 of the ring 30 has a pip or bead 74 which serves two purposes, firstly to close off a crevice such as crevice 76 in FIG. 1 which may exist between the bag wall 10 and the coupling element 12 and secondly to hold the ring 32 assembled to the coupling element 12 and to provide a liquid seal between these two parts. A like pip or bead 74 may also be included on the flexible chute ring 64 of FIG. 4.

It will be appreciated that in use there is a passage of faecal material through the stomal orifice 20 and it can readily be seen from FIGS. 1 and 2 that the chute portion 32 of the flexible ring 30 entirely eliminates or greatly reduces any chance of such faecal material becoming trapped or lodged in or on the coupling elements 12 and 14, in particular in the spaces indicated at 80 and 82 in FIG. 1. In addition, the presence of the flexible ring 30 and the arrangement of the securing welds 42 and 46 is highly advantageous in enabling a wearer to conveniently and effectively couple the two coupling elements 12 and 14 together, without any substantial pressure being applied on tender areas of the body in the peristomal region. It will also be appreciated that the flexible ring 30 could be secured to the film 40 and to the coupling element 14 by means other than plastics welding, for example by a suitable adhesive and the present invention is not to be regarded as limited to an arrangement in which a plastics welding operation is used for these purposes.

FIG. 8 diagrammatically illustrates one possible method of manufacture of an ostomy appliance using an alternative design of flexible ring 90. A bag side coupling element is shown at 92 and a body side coupling element at 94. A pad of medial grade adhesive is shown at 96 having a plastics film layer 98 secured thereto.

As stated, the manufacture would be conducted with the bag side coupling element 92 not present, and the first operation is to make a plastics weld between the flange 100 of the coupling element 94 and an annular portion 102 of the flexible ring 90. As a second plastics welding operation, an annular region 104 of the flexible ring 90 is welded to the confronting annular zone 98A of the plastics film 98. This embodiment of the invention differs from that shown in FIGS. 1 and 2 in that the flexible ring 90 does not have a chute portion corresponding to chute portion 22 of the ring 30. The assembly procedure shown in FIG. 8, could equally well be employed with a flexible ring such as ring 30 which does have a chute portion. For certain wearers, particularly those where the nature of the discharge is less likely to lead to clogging problems, a flexible intervening ring of the kind illustrated by 90 will be suitable.

I claim:

1. A body side coupling for an ostomy appliance which includes a pad of medical grade adhesive, a coupling ring, and a flexible ring located between the pad and the coupling ring, the flexible ring extending outwardly radially of the coupling beyond the coupling ring and having a chute portion located to prevent discharged material from lodging in crevices formed when said body side coupling ring is assembled together with a mating coupling ring attached to an ostomy bag portion of said ostomy appliance and between said flexible ring and said body side coupling ring, said flexible ring secured to the adhesive pad adjacent said chute portion at a first annular region which is radially inwardly of the coupling ring with respect to the coupling axis of the mating coupling rings and secured to the coupling ring at a second annular region which is spaced apart and radially outwardly of the first annular region.

2. A body side coupling according to claim 1 wherein the flexible ring further comprises means for increasing the flexibility of the flexible ring located intermediate said first and second annular regions whereby the interposing of a finger or thumb of a wearer between the flexible ring and the pad is facilitated.

3. The body side coupling of claim 2 wherein said flexibility means comprises a bend in said flexible ring.

4. The body side coupling of claim 2 wherein said flexibility means comprises a notch in said flexible ring.

5. The body side coupling of claim 2 wherein said flexibility means comprises a thin region in said flexible ring.

6. The body side coupling of claim 1 wherein said flexible ring comprises a marginal bead on said chute portion disposed to fit within and seal off an outer peripheral crevice formed where the mating coupling attaches to the ostomy bag.

7. The body side coupling of claim 1 wherein said flexible ring further comprises an intermediate portion connecting a radially outwardly extending flange portion to said chute portion, the connection of said intermediate portion to said flange portion forming a step configuration.

8. A method of making a body side coupling for use in ostomy applications comprising:
  welding a coupling element to a flexible chute ring at a first annular region; and
  welding said flexible, chute ring to a polymeric film covering of an adhesive pad at a second annular region located radially inwardly of said coupling element and first annular region adjacent a chute portion of said flexible chute ring.

9. The method of claim 8 wherein said method further comprises the step of adding a region of increased flexibility to said flexible chute ring radially outwardly adjacent said second annular region.

10. The method of claim 9 wherein said method further comprises forming a bend or notch in said flexible chute ring.

11. The method of claim 9 wherein said method further comprises forming a thin region in said flexible chute ring.

12. The method of claim 8 wherein said method further comprises forming a marginal bead on said chute portion of said flexible chute ring.

* * * * *